(12) United States Patent
Kovach et al.

(10) Patent No.: US 8,961,602 B2
(45) Date of Patent: Feb. 24, 2015

(54) ADJUSTMENT SUTURE MARKERS FOR ADJUSTABLE ANNULOPLASTY RING

(71) Applicant: St. Jude Medical, Cardiology Division, Inc., St. Paul, MN (US)

(72) Inventors: Melinda K. Kovach, Plymouth, MN (US); Rebecca Volovsek, Hudson, WI (US); XueMei Li, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 13/747,957

(22) Filed: Jan. 23, 2013

(65) Prior Publication Data

US 2013/0197632 A1    Aug. 1, 2013

Related U.S. Application Data

(60) Provisional application No. 61/591,528, filed on Jan. 27, 2012.

(51) Int. Cl.
*A61F 2/24*    (2006.01)
(52) U.S. Cl.
CPC ....... *A61F 2/2445* (2013.01); *A61F 2250/0007* (2013.01); *A61F 2250/001* (2013.01); *A61F 2250/0097* (2013.01); *A61F 2250/0098* (2013.01)
USPC .......................... 623/6.37; 623/6.36; 623/2.38

(58) Field of Classification Search
CPC ... A61F 2/2466; A61F 2/2445; A61F 2/2448; A61F 2/2457; A61L 27/16
USPC ................................................ 623/2.36–2.38
See application file for complete search history.

(56) References Cited

U.S. PATENT DOCUMENTS 5,201,880 A  *  4/1993  Wright et al. ................ 623/2.37
2010/0063586 A1*  3/2010  Hasenkam et al. .......... 623/2.37

* cited by examiner

*Primary Examiner* — Thomas J Sweet
*Assistant Examiner* — Tiffany Shipmon
(74) *Attorney, Agent, or Firm* — Lerner, David, Littenberg, Krumholz & Mentlik, LLP

(57) ABSTRACT

An adjustable annuloplasty ring includes a body in the form of an endless loop having an internal lumen therethrough, an adjustment suture extending through at least a portion of the internal lumen, a first portion of the suture exiting the lumen through a first opening in the body and a second portion of the suture exiting the lumen through a second opening in the body, and a first adjustment marker on the first portion of the suture outside of the body. The suture may be adapted to reduce the length of the body around the loop when tightened.

13 Claims, 1 Drawing Sheet

ADJUSTMENT SUTURE MARKERS FOR ADJUSTABLE ANNULOPLASTY RING

CROSS-REFERENCE TO RELATED APPLICATION

This application claims the benefit of the filing date of U.S. Provisional Patent Application No. 61/591,528 filed Jan. 27, 2012, the disclosure of which is hereby incorporated by reference herein.

BACKGROUND OF THE INVENTION

The present invention is related to prosthetic heart valve replacement, and more particularly to an adjustable annuloplasty ring.

During a mitral or a tricuspid valve repair, an adjustable annuloplasty ring may be used to repair the native valve annulus of a patient by returning that annulus to its natural anatomical shape or at least general size. An adjustment suture may be used to adjust the circumferential size of the annuloplasty ring so as to customize the annuloplasty ring to the particular, desired, native valve annulus size. By pulling on one or both ends of the adjustment suture, for example, the circumferential size of the annuloplasty ring may be reduced. By releasing one or both ends of the adjustment suture, the circumferential size of the annuloplasty ring may be increased.

Despite the various improvements that have been made to annuloplasty rings, conventional annuloplasty rings suffer from some shortcomings. There therefore is a need for further improvements to devices and methods regarding adjustable annuloplasty rings.

BRIEF SUMMARY OF THE INVENTION

An adjustable annuloplasty ring and a method of adjusting a length of an annuloplasty ring are disclosed.

An adjustable annuloplasty ring may include a body in the form of an endless loop having an internal lumen therethrough, an adjustment suture extending through at least a portion of the internal lumen, and a first adjustment marker on a first portion of the suture outside of the body. The first portion of the suture may exit the lumen through a first opening in the body. A second portion of the suture may exit the lumen through a second opening in the body. The suture may be adapted to reduce the length of the body around the loop when tightened.

The first opening may be spaced from the second opening. The adjustable annuloplasty ring may further include a second adjustment marker on the second portion of the suture outside of the body. The first adjustment marker may be formed from a material applied to a surface of the suture. The material may be selected from the group consisting of ink, paint, and an adhesive. The first adjustment marker may be formed by a permanent deformation on a surface of the suture. The permanent deformation may be a burn mark. The first adjustment marker may be formed by a stitch on a surface of the suture.

The first adjustment marker may be formed by an O-ring extending circumferentially around a surface of the suture. The first adjustment marker may be formed by a biocompatible clip clamped to the suture. The first adjustment marker may be formed by a heat-shrinkable material extending circumferentially around a surface of the suture. The first adjustment marker may include a radiopaque compound. The adjustable annuloplasty ring may further include at least one marker on a surface of the body. The adjustable annuloplasty ring may further include a plurality of markers on a surface of the body.

A method of adjusting a length of an annuloplasty ring may include providing an annuloplasty ring including a body in the form of an endless loop having an internal lumen therethrough and tightening an adjustment suture to reduce the length of the body around the loop. The adjustment suture may extend through at least a portion of the internal lumen. A first portion of the suture may exit the lumen through a first opening in the body. A second portion of the suture may exit the lumen through a second opening in the body. A first adjustment marker may be included on the first portion of the suture outside of the body. The tightening of the suture may move the first adjustment marker away from the first opening.

The first opening may be spaced from the second opening. The method may further include fastening the first portion of the suture to the second portion of the suture against the body. The second portion of the suture outside of the body may include a second adjustment marker. The first adjustment marker may be formed from a material applied to a surface of the suture. The material may be selected from the group consisting of ink, paint, and an adhesive. The first adjustment marker may be formed by a permanent deformation on a surface of the suture. The permanent deformation may be a burn mark.

The first adjustment marker may be formed by a stitch on a surface of the suture. The first adjustment marker may be formed by an O-ring extending circumferentially around a surface of the suture. The first adjustment marker may be formed by a biocompatible clip clamped to the suture. The first adjustment marker may be formed by a heat-shrinkable material extending circumferentially around a surface of the suture. The first adjustment marker may include a radiopaque compound.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

Figure 1:
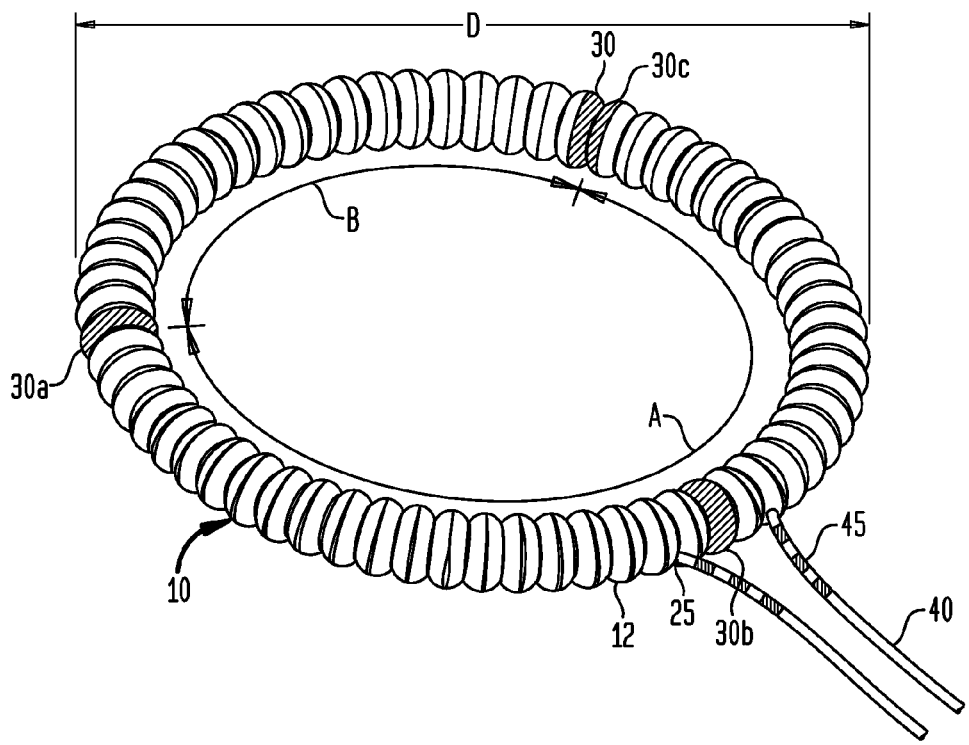
FIG. 1 is a perspective view of an adjustable annuloplasty ring having a suture including adjustment markers according to one embodiment of the invention.

FIG. 1 shows a perspective view of an adjustable annuloplasty ring 10 having an adjustment suture 40 including adjustment markers 45. Ring 10 may be formed from any biocompatible material suitable for implantation into a valve annulus of a patient and that is also adjustable in ring size (as described below) to help achieve and maintain a desired circumferential dimension of the patient's native valve annulus.

A user may visualize ring 10 directly or on a video screen, with or without magnification. Ring 10 may be implanted robotically, using a minimally invasive approach, or may be implanted otherwise using conventional techniques. Ring 10 also may include any suitable number of markers 30 to visually aid a user of the ring in spacing sutures evenly around the ring and annulus during implantation (e.g., when suturing the ring into the annulus). Markers 30 may be formed with any geometric shape, and may include a line of any suitably visible width and length, a dotted line, a dot, a circle, or any other suitably visible configuration. Markers 30 may include one or more marks on ring 10 made using ink, dye, or colored yarn that is weaved or knitted into the ring at desired positions around the circumference of the ring. In a particular embodiment, markers 30 may indicate the boundaries of adjustability of ring 10. For example, an arcuate portion A of ring 10 extending around about ⅔ of the circumference of the ring from marker 30a, past marker 30b, to marker 30c may be adjustable as described below, and a remaining arcuate portion B of ring 10 extending around about ⅓ of the circumference of the ring may be non-adjustable.

A portion of adjustment suture 40 may be located in the internal channel or lumen of ring 10, and the remainder of the adjustment suture may be located outside of ring 10. Adjustment suture 40 may enter and exit ring 10 through openings 25 extending through an outwardly-facing surface 12 of the ring. For example, inside ring 10, suture 40 may continue the long way around the ring between openings 25. In other words, the portions of adjustment suture 40 that are visible in FIG. 1 may be part of one continuous suture strand, with the connection between the two portions visible outside of ring 10 extending the long way around the lumen of the ring from one opening 25 to the other opening.

Adjustment suture 40 may be formed from any suitable biocompatible material that is capable of adjusting the dimensions of ring 10. If a user pulls one or both ends of adjustment suture 40 to expose more of the adjustment suture, the materials that comprise ring 10 may compress, thereby reducing the diameter D of the ring. Ring 10 may be formed from a pleated natural so as to compress in a known and repeatable manner. If the user releases one or both ends of adjustment suture 40 and gently applies a radially outward force on ring 10, or otherwise permits more of the adjustment suture to be positioned within the ring, the materials that comprise the ring may re-expand, thereby increasing the diameter D of the ring. When ring 10 has been adjusted (using one or both ends of adjustment suture 40) to have the desired final diameter D in the patient, that size of the ring can be fixed (e.g., made permanent), for example, by tying tightly together (immediately adjacent to the ring) the portions of adjustment suture 40 that emerge from the ring.

In one embodiment, portions of suture 40 may be attached to ring 10 inside the ring at markers 30a and 30c, such that when a user pulls one or both ends of the suture to expose more of the suture, ring 10 may be circumferentially compressed only within the arcuate portion A thereof, with the remaining portion B of the ring remaining uncompressed. In another embodiment, suture 40 may include two separate suture strands, wherein a first end of a first suture strand is attached to ring 10 inside the ring at marker 30a and a second end thereof extends outside of the ring through a first opening 25, and a first end of a second suture strand is attached to ring 10 inside the ring at marker 30c and a second end thereof extends outside of the ring through a second opening 25. In such an embodiment including two separate suture strands, when a user pulls the exposed second end of one or both suture strands to expose more of the suture 40, ring 10 may be circumferentially compressed only within the arcuate portion A thereof, with the remaining portion B of the ring remaining uncompressed.

Although ring "diameter" is sometimes mentioned herein as a measure of ring size, it will be understood that, when implanted in a patient, ring 10 may not remain a perfect circle with one uniform diameter in all radial directions. Rather, the ring may become somewhat oval, elliptical, D-shaped, or the like, and may also not have all of its parts lying in one plane. An alternative way to describe the effect on ring size of pulling on (tensioning) or loosening adjustment suture 40 may be to refer to the perimeter size, the circumferential size, or the annular size of the ring. By each of these terms it is meant that the distance around ring 10 (e.g., the long way around the ring from one opening 25 to the other opening) can be decreased by tightening adjustment suture 40 or increased by loosening that suture. Such distance change respectively decreases or increases the perimeter size, the circumferential size, the annular size, or the like of ring 10, and is analogous to what is elsewhere referred to herein as a change in the size of ring diameter D. Thus, references herein to changes in diameter D should be understood to be a simplified way of describing what may be more generally thought of as a change in ring circumference, perimeter, or the like.

One or more adjustment markers 45 are located on adjustment suture 40 to aid a user in observing the position or the movement of the adjustment suture relative to ring 10 during the ring diameter adjustment process. Adjustment markers 45 may be beneficial during or after adjustment of diameter D of ring 10 because direct and/or accurate observation of the size of the ring may be more difficult than direct and/or accurate observation of the location of the adjustment markers relative to the ring. Adjustment suture 40 preferably includes at least one adjustment marker 45 in a location where the adjustment marker is directly visible to the eye of a user, or visible in a camera projection or image of a surgical area with or without magnification.

Adjustment markers 45 may indicate to the user how much ring 10 has been adjusted (either tightened or loosened), whether the ring is being adjusted at any particular moment, and whether the adjustment is holding properly. For example, if ring 10 is tightened above a predetermined tension force, adjustment suture 40 may loosen after implantation, thereby increasing diameter D. Such an increase in diameter D may be difficult to observe without the use of adjustment markers 45. Adjustment markers 45 may be arranged to give an accurate indication of the size to which ring 10 has been adjusted. For example, depending on which of adjustment markers 45 and/or how many of the adjustment markers are visible outside of ring 10, a user can tell from observation of those markers the current diameter D of the ring.

Adjustment markers 45 may include one or more biocompatible markings of any color(s), shape(s), or pattern(s) suitably visible to a user either directly or on a video screen, with or without magnification (e.g., in a blood field). Adjustment markers 45 should not interfere with the implantation, adjustability, or final adjustment (e.g., suture tying) of ring 10. The geometry of each adjustment marker 45 may include a line of any suitably visible width (e.g., a short line on one side of adjustment suture 40 or a line that travels the circumference of the adjustment suture), a dotted line, a dot, a circle, or any other suitably visible configuration.

Adjustment markers 45 may include one or more marks on adjustment suture 40 made using ink, a tissue marker, a permanent marker, paint, or an adhesive. Alternatively, adjustment markers 45 may include one or more marks "burned" into adjustment suture 40 using any suitable device, such as a laser, a heated metal wire, or another metal object. Adjustment markers 45 may be stitches of a smaller suture that are applied to (e.g., stitched onto, wrapped around) adjustment suture 40, having a color or colors contrasting with the color of the adjustment suture. The smaller suture stitches may include a variety of patterns, such as an "X" pattern, an asterisk pattern, or a pattern including a series of lines or overlapping stitches.

Figure 2:
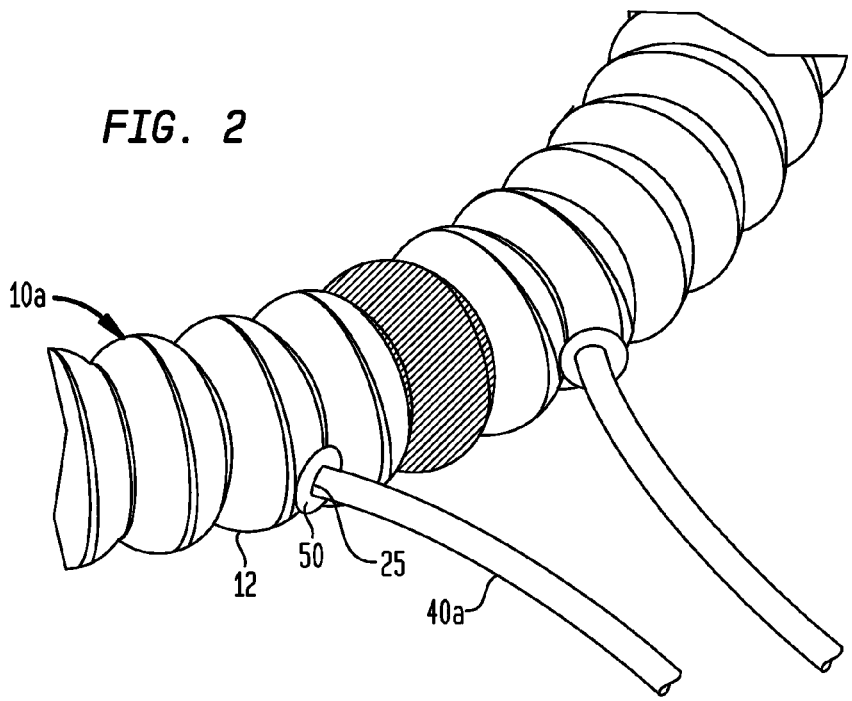
FIG. 2 is an enlarged partial view of a portion of an adjustable annuloplasty ring according to another embodiment of the invention having adjustment O-rings.

In some embodiments, alternate adjustment markers (or each individual adjustment marker) may be components that are distinct structures that are joined to an adjustment suture. Such a component may be a tube or an o-ring, made from one or more biocompatible materials (e.g., silicone) and placed over an adjustment suture. For example, referring now to FIG. 2, an alternative embodiment of an adjustable annuloplasty ring 10a has an adjustment suture 40a including adjustment O-rings 50. O-rings 50 may be formed from silicone and include a radiopaque compound, such as barium sulfate. O-rings 50 may have a white color that may contrast with a colored (e.g., non-white) adjustment suture 40. Although adjustment O-rings 50 are shown in FIG. 2, any other alternative adjustment marker (e.g., a tube) may be used in place of the O-rings in any embodiment or variation thereof described herein.

One or more adjustment O-rings 50 may be positioned anywhere along the length of adjustment suture 40a. For example, as shown in FIG. 2, adjustment O-rings 50 are initially located against outwardly-facing surface 12 of ring 10a at openings 25. During the initial assembly of ring 10a, adjustment O-rings 50 may be movable with respect to adjustment suture 40a, such that the adjustment O-rings may be positioned in locations that are desired by a user. After the initial assembly of ring 10a, adjustment O-rings 50 may not move relative to adjustment suture 40a when ring 10a is shaken or when the adjustment suture is tightened or loosened. Adjustment O-rings 50 may be secured to adjustment suture 40a by a method such as adhesive bonding, melting, or sewing. Adjustment O-rings 50 should not noticeably interfere with the tying of adjustment suture 40a to fix diameter D of ring 10a.

In some embodiments, O-rings 50 may be replaced by one or more biocompatible clips, such as a metallic clip including nitinol or titanium. Examples of such clips may include ligation clips (e.g., Vitaclip®), U-clips (e.g., Coalescent U-Clip™), and clips or clamps that are otherwise used for microvascular procedures.

In some embodiments, O-rings 50 may be replaced by a heat-shrinkable material that is deposited or placed in another manner over adjustment suture 40a. Examples of such heat-shrinkable materials may include polytetrafluoroethylene (PTFE), fluorinated ethylene propylene (FEP), or any other suitable material.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, other methods of marking adjustment sutures 40 and 40a to visualize the adjustment of annuloplasty rings 10 and 10a may occur to those skilled in the art.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An adjustable annuloplasty ring, comprising:
   a body in the form of an endless loop having an internal lumen therethrough;
   an adjustment suture extending through at least a portion of the internal lumen, a first portion of the suture exiting the lumen through a first opening in the body and a second portion of the suture exiting the lumen through a second opening in the body, the suture adapted to reduce the length of the body around the loop when tightened; and
   a plurality of first adjustment markers on the suture, the first adjustment markers spaced apart from one another along the length of the suture, the first adjustment markers arranged to move from inside the body when the body has a first diameter to outside the body when the body has a second diameter smaller than the first diameter, the first adjustment markers having locations along the suture arranged to indicate the value of the second diameter.

2. The adjustable annuloplasty ring of claim 1, wherein the first opening is spaced from the second opening.

3. The adjustable annuloplasty ring of claim 2, further comprising a second adjustment marker on the second portion of the suture outside of the body.

4. The adjustable annuloplasty ring of claim 1, wherein the first adjustment marker is formed from a material applied to a surface of the suture, the material being selected from the group consisting of ink, paint, and an adhesive.

5. The adjustable annuloplasty ring of claim 1, wherein the first adjustment marker is formed by a permanent deformation on a surface of the suture.

6. The adjustable annuloplasty ring of claim 5, wherein the permanent deformation is a burn mark.

7. The adjustable annuloplasty ring of claim 1, wherein the first adjustment marker is formed by a stitch on a surface of the suture.

8. The adjustable annuloplasty ring of claim 1, wherein the first adjustment marker is formed by an O-ring extending circumferentially around a surface of the suture.

9. The adjustable annuloplasty ring of claim 1, wherein the first adjustment marker is formed by a biocompatible clip clamped to the suture.

10. The adjustable annuloplasty ring of claim 1, wherein the first adjustment marker is formed by a heat-shrinkable material extending circumferentially around a surface of the suture.

11. The adjustable annuloplasty ring of claim 1, wherein the first adjustment marker includes a radiopaque compound.

12. The adjustable annuloplasty ring of claim 1, further comprising at least one marker on a surface of the body.

13. The adjustable annuloplasty ring of claim 12, further comprising a plurality of markers on a surface of the body.

* * * * *